(12) United States Patent
Masuzawa et al.

(10) Patent No.: US 7,483,557 B2
(45) Date of Patent: Jan. 27, 2009

(54) MEDICAL IMAGING COMMUNICATION SYSTEM, METHOD AND SOFTWARE

(75) Inventors: Takashi Masuzawa, Otawara (JP); Akihiro Toshimitsu, Otawara (JP); Takashi Ichihara, Otawara (JP)

(73) Assignees: Kabushiki Kaisha Toshiba, Tokyo (JP); Toshiba Medical Systems Corporation, Tochigi-Ken (JP)

(*) Notice: Subject to any disclaimer, the term of this patent is extended or adjusted under 35 U.S.C. 154(b) by 767 days.

(21) Appl. No.: 10/949,690

(22) Filed: Sep. 24, 2004

(65) Prior Publication Data
US 2005/0080330 A1    Apr. 14, 2005

(30) Foreign Application Priority Data
Sep. 30, 2003    (JP)    ............. 2003-339118

(51) Int. Cl.
*G06K 9/001* (2006.01)
(52) U.S. Cl. ............. 382/131; 382/157; 378/4
(58) Field of Classification Search ............. 382/100, 382/128, 129, 130, 131, 132, 154, 155, 168, 382/181, 209, 224, 232, 260, 274, 276, 294–299, 382/305, 318, 133, 134, 157, 189; 378/19, 378/4; 707/104.1; 345/668
See application file for complete search history.

(56) References Cited

U.S. PATENT DOCUMENTS

| | | | | |
|---|---|---|---|---|
| 4,833,625 A | * | 5/1989 | Fisher et al. | 345/668 |
| 6,260,021 B1 | * | 7/2001 | Wong et al. | 705/2 |
| 6,691,134 B1 | * | 2/2004 | Babula et al. | 707/104.1 |
| 6,748,044 B2 | * | 6/2004 | Sabol et al. | 378/4 |
| 7,054,409 B2 | * | 5/2006 | Ross et al. | 378/19 |
| 7,274,810 B2 | * | 9/2007 | Reeves et al. | 382/128 |

FOREIGN PATENT DOCUMENTS

| | | | |
|---|---|---|---|
| JP | 08-315119 | * | 11/1996 |
| JP | 10-137231 | | 5/1998 |
| JP | 2002-230165 | | 8/2002 |
| JP | 2003-102721 | | 4/2003 |

* cited by examiner

*Primary Examiner*—Seyed Azarian
(74) *Attorney, Agent, or Firm*—Knoble Yoshida & Dunleavy, LLC

(57) ABSTRACT

The picture archiving and communication system (PACS) substantially optimizes a post-scanning command process in accordance with a user-specified priority for further processing a selected set of imaging data that has been collected by medical imaging devices such as a CT scanner and a MRI scanner and stored in distributed storage units on the network. The user-specified priority includes the least response time, the least costs and the least network traffic. The user-specified priority is optionally fixed in some preferred embodiments.

40 Claims, 16 Drawing Sheets

FIG.13

TABLE 1

PROCESSOR A

| DATA SIZE | 512K | 1024K | 1536K | . . . . |
|---|---|---|---|---|
| PROGRAM A | 0.1mSec | 0.2mSec | 0.3mSec | |
| PROGRAM B | 0.15mSec | 0.28mSec | 0.44mSec | |
| PROGRAM C | 0.2mSec | 0.4mSec | 0.6mSec | |
| ⋮ | | | | |

FIG.14

TABLE 2

FILE SERVER A

| ID | DATA SIZE | SCANNED DATE | LOCATION | . . . |
|---|---|---|---|---|
| 1 | 400MB | 01/02/04 | C:XX/YY/z.dat | |
| 2 | 600MB | 02/01/04 | C:XX/YY/f.dat | |
| D | 10MB | 02/00/04 | C:XX/YY/d.dat | |
| ⋮ | | | | |

FIG.15

TABLE 3
PROGRAM INFO

| PROGRAM ID | PROCESSING DESCRIPTION | PROGRAM SIZE(MB) | STANDARD PPROCESSING TIME(SEC) | PROGRAM LOCATION |
|---|---|---|---|---|
| 1 | CAD-TEMPORAL SUBTRACTION | 5 | 45 | D:XX/Y/ |
| 2 | 3D-MPR | 10 | 30 | E:YY/Z/ |
| 3 | 3D-SHADED SURFACE RENDERING | 15 | 60 | F:Z/dd/ |

FIG.16

TABLE 4

| IMAGE FILE SERVER | IMAGE DATA D | PROCESSING PROGRAM 2 | CPU UTILIZATION % |
|---|---|---|---|
| IMAGE FILE SERVER a | × | ○ | 50 |
| IMAGE FILE SERVER b | ○ | × | 20 |
| IMAGE FILE SERVER c | × | × | 50 |
| IMAGE FILE SERVER e | ○ | × | 20 |
| MOBILE TERMINAL f | × | ○ | 0 |

FIG.17

TABLE 5

| IMAGE FILE SERVER | RELATIVE CPU PERFORMANCE LEVEL % | MEMORY SIZE (MB) |
|---|---|---|
| IMAGE FILE SERVER a | 100 | 1024 |
| IMAGE FILE SERVER b | 50 | 1024 |
| IMAGE FILE SERVER c | 200 | 2048 |
| IMAGE FILE SERVER e | 100 | 1024 |
| MOBILE TERMINAL f | 40 | 256 |

FIG.18

TABLE 6

| SEGMENTS | TRANSMISSION RATE (Mbps) |
|---|---|
| LH | 1000 |
| LH-SH | 50 |
| SH | 100 |
| LH-M | 10 |
| SH-M | 10 |

FIG.19

TABLE 7

| SEGMENTS | IMAGING DATA TRANSMISSION TIME (SEC) | PROCESSING PROGRAM TRANSMISSION TIME (SEC) | PROCESSED IMAGING DATA TRANSMISSION TIME (SEC) |
|---|---|---|---|
| LH | 2.4 | 0.08 | 0.04 |
| LH-SH | 48 | 1.6 | 0.8 |
| SH | 24 | 0.8 | 0.4 |
| LH-M | 240 | 8 | 4 |
| SH-M | 240 | 8 | 4 |

FIG. 20

TABLE 8

| IMAGE FILE SERVER | IMAGING DATA TRANSMISSION TIME | SEGMENTS | PROCESSING PROGRAM TRANSMISSION TIME | SEGMENTS | CPU PROCESSING TIME | PROCESSING IMAGING DATA TRANSMISSION TIME | TOTAL RESPONSE TIME |
|---|---|---|---|---|---|---|---|
| IMAGE FILE SERVER a | 2.4 | LH | 0 | N/A | 60 | 4 | 66.4 |
| IMAGE FILE SERVER b | 0 | N/A | 0.08 | LH | 75 | 4 | 79.08 |
| IMAGE FILE SERVER c | 2.4 | LH | 0.08 | LH | 30 | 4 | 36.48 |
| IMAGE FILE SERVER e | 0 | N/A | 1.6 | LH-SH | 37.5 | 4 | 48.1 |
| MOBILE TERMINAL f | 240 | SH-M | 0 | N/A | 75 | 4 | 31.9 |

MEDICAL IMAGING COMMUNICATION SYSTEM, METHOD AND SOFTWARE

FIELD OF THE INVENTION

The current invention is generally related to medical imaging, and more particularly related to a system, software, method and apparatus for substantially optimizing a post-scanning command process in a picture archiving and communication system (PACS).

BACKGROUND OF THE INVENTION

In the recent years, computer technologies have brought hospitals and clinics the advanced use of the computer systems. At most large hospitals, the hospital information system has been installed. Similarly, the medical imaging devices have been widely used and include X-ray computer tomography (CT) scanners, Positron Emission CT Scanners, magnetic resonance imaging (MRI) devices and digital X-ray devices.

Despite the widespread use of imaging devices, the stored image data is not managed by a computer system at many institutions. Rather, the medical images are still viewed on traditional hard-copy media such as films. For a traditional medical image management, the following problems are associated. It generally takes some time to retrieve a desired hard copy. As a result of a large storage volume, it requires a large physical storage area, and a film is often lost.

To solve the above problems, the picture archiving and communication system (PACS) has been developed. For example, TOSPACS view (TWS-2000) is commercially available from Toshiba Medical Systems. In general, the PACS enables that the medical imaging data is stored in a database at a file server or other storage devices while a desired image is accessed on line via network from an office, an outpatient clinic and a hospital.

Furthermore, the use of the medical image is combined with the computer aided diagnosis (CAD). A certain portion of the scanned image is processed by a predetermined software program to isolate an abnormal area. In the above described use, the PACS is used to obtain the desired image data via a network from the file server for preparing an input to the CAD. Thus, the environment includes a file server at every medical facility for storing imaging data that has been collected from medical imaging devices such as an X-ray device, a CT scanner and a MRI scanner. The environment also includes a central facility where a predetermined set of processing software is centrally deposited and managed. For example, the software processes the scanned image data to generate a three-dimensional image, a combined image of selected portions and arranged images. Lastly, the environment further includes a cluster of distributed viewing terminals or consoles where an authorized user requests a specific imaging data and issues a desired post-scanning processing command via the network for further processing the requested imaging data.

In the above described distributed environment, the system is not responsive in certain situations. In response to a request to process a specified imaging data set from a viewing console, a central control device determines a file server where the specified imaging data is stored and transmits the file server a request to transfer the specified imaging data to the central device. The central device performs a specified post-scanning process on the transferred imaging data and transmits the processed imaging data back to the viewing console. Because of the voluminous nature of the medical imaging data, a large amount of data is transferred over the network between the file server and the central device. Although the imaging data can be transferred in advance of a certain post-scanning process to minimize the response time, it is not possible to anticipate every post-scanning process. As a result of the increased network traffic, a response time at the viewing console becomes undesirable.

In relation to the prior art, the following disclosures teach some specific techniques for improving some aspects of the above described problems. Japanese Patent Publication 2002-230165 discloses a picture archiving and communication system. After access from a viewing terminal is authorized at an image data storage facility, the viewing terminal receives not only requested medical imaging data in a compressed format but also a predetermined viewing program. The downloaded software such as a JAVA applet enables only an authorized user to view a requested medical image by decoding and decompressing the downloaded imaging data. The authorized user is able to generate a report and upload it in an encoded and or compressed format. After the access is complete, the downloaded JAVA applet is disabled or deleted at the viewing terminal.

Japanese Patent Publication 2003-102721 discloses a picture archiving and communication system. Medical imaging data is locally collected at a client device or a modality and is centrally stored in a file server via a network. A user retrieves a medical image from the file server for viewing at a local terminal that is connected to the file server via the network. During the viewing, the user issues a post-scanning process command including parameters indicative of certain commands such as noise reduction or edge enhancement of the X-ray scanned imaging data. In response to the post-scanning process command, the system determines a client device that currently has the lightest processing load and is capable of processing the requested post-scanning process. The selected client device receives the specified imaging data from the central file server. Since each one of the client devices has a local copy of the processing software programs, it performs the specified post-scanning process. The processed image data is delivered and stored at a requested storage address in the parameter.

Japanese Patent Publication Hei 8-315119 discloses a picture archiving and communication system. Medical imaging data is locally collected at a client device or a modality and is centrally stored in a file server via a network. To avoid a duplicate medical image at a central storage unit, an incoming image for storage is checked based upon a certain combination of predetermined sets of criteria such as an ID number attached to the image, a time stamp of the image and or a difference between images. The substantially reduced duplicate image data enables the storage unit to efficiently store the image data as well as efficiently transfer the requested imaging data over the network without a duplicate.

Despite the above described prior art attempts, the PACS remains to be desired for optimizing the post-scanning process command. Since the PACS environment is not static and the user priority varies, the PACS should be able to optimize the post-scanning processing in a flexible and a cost-efficient manner without increasing network traffic and response time.

SUMMARY OF THE INVENTION

In order to solve the above and other problems, according to a first aspect of the current invention, a method of archiving, processing and communicating imaging data over a network, including the steps of: storing processing software programs at a second device on the network; storing imaging data at a first device on the network; requesting the second device for information on a medical image from a third device on the network; requesting a process to be performed on imaging data for the requested medical image from the third device if the imaging data needs to be processed; transferring from the second device the information to the first device; transferring from the second device a selected one of the processing software programs associated with the requested process to the first device if the process has been requested; and executing the transferred processing software program to process the imaging data at the first device to generate processed imaging data for a processed medical image if the process has been requested.

According to a second aspect of the current invention, a method of archiving, processing and communicating imaging data over a network, a mobile device on the network storing processing software programs, a first device on the network storing imaging data and associated information, a second device on the network storing processing software programs and imaging data, including the steps of: requesting the first device for the associated information from the mobile device; displaying the associated information at the mobile device; selecting at least one medical image based upon the associated information at the mobile device; receiving at the mobile device a portion of imaging data for the selected medical image from the first device; selecting at the mobile device a process to be performed by one of the processing software programs on the imaging data; in response to the decision result, inquiring of the second device about the existence of the selected medical image and the software program corresponding to the selected process at the second device to receive an inquiry result; transferring to the second device from the mobile device a combination of information on the selected medical image and the software program for the selected process based upon the inquiry result; and executing the transferred software program to process the imaging data for the selected medical image at the second device to generate processed imaging data.

According to the third aspect of the current invention, a method of archiving, processing and communicating imaging data over a network, including the steps of: maintaining first information on processing software programs on the network; maintaining second information on a plurality of medical imaging data on the network; requesting the first information on a selected one of the medical imaging data located at a first device on the network; requesting the second information on a selected one of the processing software programs located at a second device to be performed on the selected imaging data; comparing the first information to the second information to generate a comparison result indicative of either the selected medical imaging data or the selected processing software program is to be transferred; transferring the selected medical imaging data to the second device or the selected processing software program to the first device based upon the comparison result; and executing the selected processing software program to process the selected imaging data to generate processed imaging data.

According to the fourth aspect of the current invention, a method of archiving, processing and communicating imaging data over a network, including the steps of: maintaining first information on static elements including processing software programs and a plurality of medical imaging data on the network; maintaining second information on dynamic elements including transmission rates on the network; issuing a post-scanning process command including a selected one of the medical imaging data located at a first device on the network to be processed by a selected one of the processing software programs located at a second device on the network as well as a user-defined priority; requesting the first information on the selected medical imaging data and the second information on the selected processing software program; optimizing the user-defined priority based upon the first information and the second information; transferring a combination of the selected medical imaging data and the selected processing software program over the network according to the optimized user-defined priority; and executing the selected processing software program to process the selected imaging data to generate processed imaging data in accordance with the optimized user-defined priority.

According to the fifth aspect of the current invention, a system for archiving, processing and communicating imaging data over a network, including: a first device on the network for storing imaging data; a second device on the network for storing processing software programs; and a third device on the network for transmitting a request to the second device for information on a medical image and a process to be performed on imaging data for the requested medical image if the imaging data needs to be processed, in response to the request, the second device transferring the information to the first device and a selected one of the processing software programs associated with the process to the first device if the process has been requested, the first device executing the transferred processing software program to process the imaging data to generate processed imaging data for a processed medical image if the process has been requested.

According to the sixth aspect of the current invention, a system for archiving, processing and communicating imaging data over a network, including: a first device on the network for storing imaging data for medical images and associated information; a second device on the network for storing the image data for the medical images and processing software programs and for processing the imaging data by the processing software programs; and a mobile device on the network for storing the processing software programs, the mobile device sending an image list request to the first device to receive the associated information, the mobile device displaying the associated information for a user to select a set of imaging data for at least one medical image and one of the processing software programs, the mobile device inquiring of the second device about the existence of the selected imaging data and the selected processing software program at the second device to receive an inquiry result, the mobile device transferring to the second device a combination of the selected imaging data and the selected processing software program based upon the inquiry result, the second device executing the transferred processing software program to process the selected imaging data to generate processed imaging data.

According to the seventh aspect of the current invention, a system for archiving, processing and communicating imaging data over a network, including: a first device on the network for storing imaging data and optionally processing the imaging data; a second device on the network for storing processing software programs and optionally processing the imaging data; a database on the network for maintaining first information on the processing software programs and second information on a plurality of the medical imaging data on the network; and a third device on the network for requesting the first information on a selected one of the medical imaging data that is located at the first device and the second information on a selected one of the processing software programs that is located at the second device to be performed on the selected imaging data, the third device comparing the first information to the second information to generate a comparison result indicative of either the selected medical imaging data or the selected processing software program is to be transferred, the first device transferring the selected medical imaging data to the second device based upon the comparison result, the second device transferring the selected processing software program to the first device based upon the comparison result, the first device or the second device executing the selected processing software program to process the selected imaging data to generate processed imaging data based upon the comparison result.

According to the eighth aspect of the current invention, a system for archiving, processing and communicating imaging data over a network, including: a first device on the network for storing medical imaging data; a second device on the network for storing processing software programs; a database on the network for maintaining first information on static elements including processing software programs and a plurality of medical imaging data on the network and for maintaining second information on dynamic elements including transmission rates on the network; a third device on the network for issuing a post-scanning process command including a user-defined priority and a selected one of the medical imaging data located at the first device to be processed by a selected one of the processing software programs located at the second device, the third device requesting the first information on the selected medical imaging data and the second information on the selected processing software program, the third device optimizing the user-defined priority based upon the first information and the second information, a combination of the selected medical imaging data and the selected processing software program being transferred over the network according to the optimized user-defined priority; the selected processing software program being executed to process the selected imaging data to generate processed imaging data in accordance with the optimized user-defined priority.

These and various other advantages and features of novelty which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

FIG. 13 is an exemplary table illustrating information on processing speed of processing programs for various data sizes in a predetermined table format to be used in the above preferred processes according to the current invention.

FIG. 14 is an exemplary table illustrating information on data size, scanned date and location of imaging data files in a predetermined table format to be used in the above preferred processes according to the current invention.

FIG. 15 is an exemplary table illustrating the information on the file size, the description, the standard processing speed and the location of the processing software in a predetermined table format to be used in the above preferred processes according to the current invention.

FIG. 16 is an exemplary table illustrating the information on the presence of the specified imaging data file and the specified processing program file as well as the CPU utilization percentage at the processing entities in a predetermined table format to be used in the above preferred processes according to the current invention.

FIG. 17 is an exemplary table illustrating the information on the relative CPU performance level and the memory size of the processing entities in a predetermined table format to be used in the above preferred processes according to the current invention.

FIG. 18 is an exemplary table illustrating the information on the transmission speed of the network segments in a predetermined table format to be used in the above preferred processes according to the current invention.

FIG. 19 is an exemplary table illustrating the information on the imaging data transmission time, the processing program transmission time and the processed imaging data transmission time for the network segments in a predetermined table format to be used in the above preferred processes according to the current invention.

FIG. 20 is an exemplary table illustrating the information on the imaging data transmission time, the first corresponding network segments, the processing program transmission time, the second corresponding network segments, the CPU processing time, the processed imaging data transmission time and the total response time for the processing entities in a predetermined table format to be used in the above preferred processes according to the current invention.

DETAILED DESCRIPTION OF THE PREFERRED EMBODIMENT(S)

Based upon incorporation by external reference, the current application incorporates all disclosures in the corresponding foreign priority document (Japanese Patent Publication 2003-339118 from which the current application claims priority.

Figure 1:
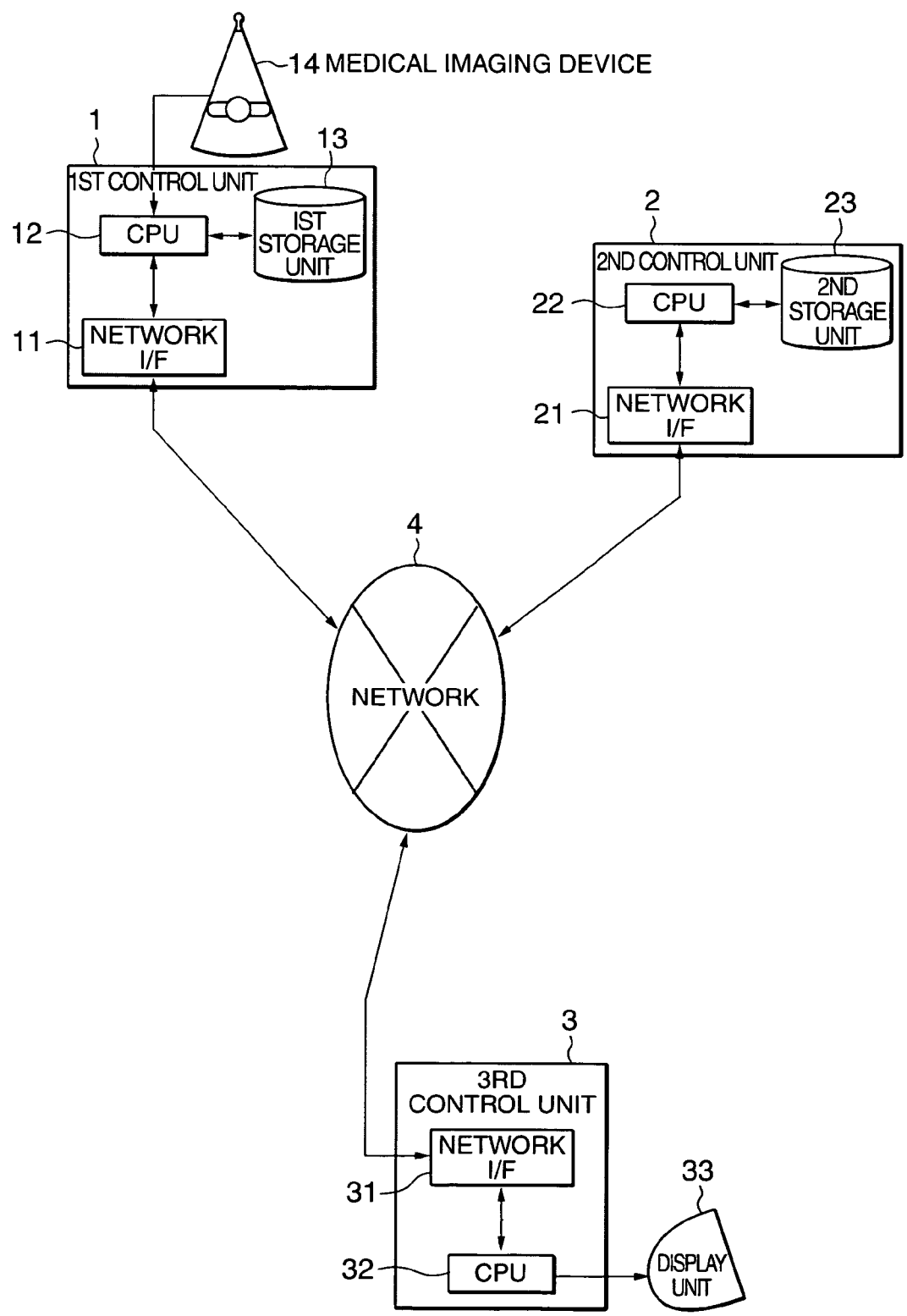
FIG. 1 is a diagram illustrating one preferred embodiment of the system for archiving, processing and communicating medical imaging data according to the current invention.

Referring now to the drawings, wherein like reference numerals designate corresponding structures throughout the views, and referring in particular to FIG. 1, a diagram illustrates one preferred embodiment of the system for archiving, processing and communicating medical imaging data according to the current invention. The system includes a first control unit 1 for controlling a medical imaging device such as a computer tomography (CT) scanner 14, a second control unit 2 for processing various tasks, a third control unit 3 for controlling a viewing terminal or console 33 and a network 4 such as a local network (LAN), an intra network and or the Internet that connects the above control units 1, 2 and 3. The first control unit 1 further includes a first central processing unit (CPU) 12 for controlling the CT scanner 14, a first storage unit 13 for storing imaging data that has been scanned by the CT scanner 14 and a first network interface (I/F) unit 11 for interfacing the first control unit 1 with the network 4. For example, the first control unit 1 is a file server that is located at every medical facility where a medical imaging device such as the CT scanner 14 is available. The first CPU 12 executes instructions to read and write imaging data to and from the storage unit 13 to function as a database server. The first CPU 12 also executes instructions to receive the imaging data from the network 4 via the network I/F 11. Then, the CPU 12 performs a certain specified process on the imaging data that is either read from the storage unit 13 or received from the network to generate processed imaging data at the first control unit 1. Lastly, the first CPU 12 transmits the processed imaging data to the network 4 via the network I/F 11 and or stores the processed imaging data back in the storage unit 13. Thus, the first control unit 1 is synonymously referred to as an image file server 1.

Still referring to FIG. 1, the second control unit 2 further includes a second central processing unit (CPU) 22 for performing a certain specified process, a second storage unit 23 for storing software programs for performing predetermined processes and a second network interface (I/F) unit 21 for interfacing the second control unit 2 with the network 4. The CPU 22 executes the stored software programs under certain conditions. One exemplary software program processes the imaging data to generate an input in a predetermined format to the CAD from the image data. Other software programs generate a three-dimensional image, a combined image of selected portions and arranged images of a certain portion. The CPU 22 also executes instructions to write or read the software programs to and from the second storage unit 23 to function as a database. Furthermore, the CPU 22 executes instructions to transmit to the network 4 the software programs that are stored in the storage unit 23. In certain situations, the CPU 22 also executes instructions to receive the imaging data from the network 4 via the network I/F unit 21. In case of receiving the image data from the network 4, the CPU 22 performs a certain specified process on the received imaging data to generate processed imaging data at the second control unit 2. The second control unit 2 generally determines how and where a requested task is processed. Although the diagram illustrates the single file server 1 and the single terminal device 3, a plurality of the file servers 1 and the terminal devices 3 is connected to the network 4 under the control of the central device unit 2. The second control unit 2 functions as a central command post for managing the imaging data that is stored in a plurality of the image file servers 1 as well as for communicating with the third control units 3. Thus, the second control unit 2 is synonymously referred to as a central device 2.

Lastly, with respect to FIG. 1, the third control unit 3 further includes a third central processing unit (CPU) 32 for controlling a display unit or console 33 and a third network interface (I/F) unit 31 for interfacing the third control unit 3 with the network 4. The display unit 33 functions as a terminal device that a user utilizes to view the medical image that is received from the network 4 via the network I/F 31. The third control unit 3 further includes an input device such as a keyboard and or a mouse to issue commands including a post-scanning process command that is transmitted to the central device 2 via the network 4. Although the third control unit 3 includes the CPU 32, the CPU 32 is optionally an inexpensive processor that does not have to be powerful enough to perform a certain process on the imaging data as specified in the post-scanning command. Thus, the third control unit 3 is synonymously referred to as a terminal device 3.

Figure 2:
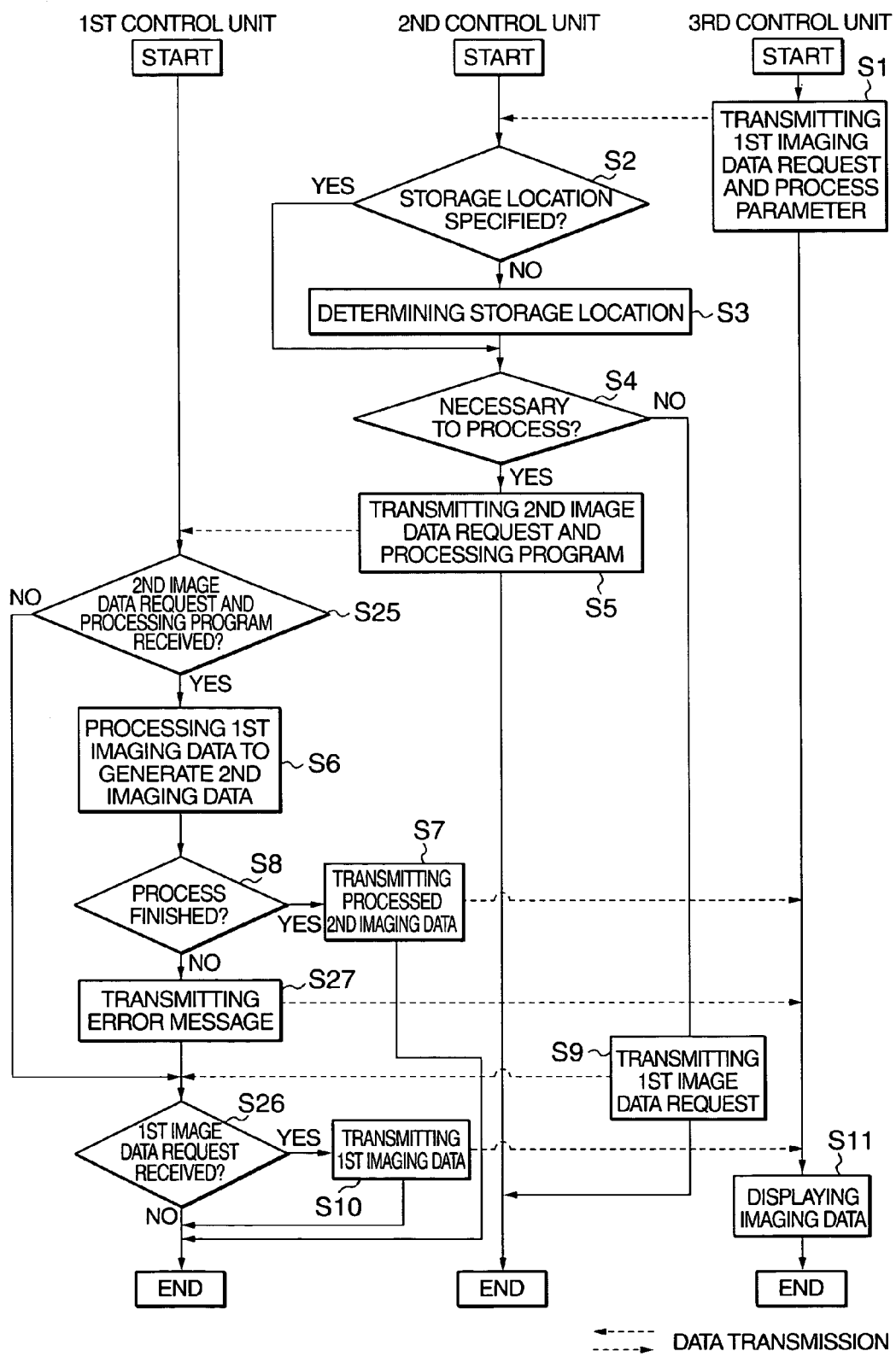
FIG. 2 is a flow chart illustrating steps that transpire among the image file server, the central device and the terminal device in one preferred process according to the current invention.

Now referring to FIG. 2, a flow chart illustrates steps that transpire among the first control unit or the image file server 1, the second control unit or the central device 2 and the third control unit or the terminal device 3 in one preferred process according to the current invention. To describe the preferred process, although the units or components of FIG. 1 are referred, the preferred process of FIG. 2 is not limited to these units or components of FIG. 1 for its implementation. It is assumed that the image file server 1, the central device 2 and the terminal device 3 are independently operating on the same network 4 at an initial stage. In the flow chart, a solid line indicates a transition between steps within the same unit while a dotted line indicates a data transmission between the units. In a step 1, the terminal device 3 transmits a first image transmission request to the central device 2 with a parameter set including an imaging data ID and or a process ID (also processing program ID). The imaging data ID may include a network address of the imaging data file or other information to identify its storage location. The parameter set may also automatically include the address of the terminal device 3 that transmits the first image transmission request, and the address is used as a return address for the requested image.

In response to the first image transmission request, the central device 2 determines in a step 2 whether or not the storage location of the requested image is specified in the first transmission request. If it is determined in the step S2 that the address is not specified in the parameter, the central device 2 determines the address of the requested imaging data file in a step S3 based upon the imaging data ID. The second control unit 2 functions as a database manager for managing a table for the location of the imaging data files that are stored in a plurality of the image file servers 1. On the other hand, if it is determined in the step S2 that the address is specified in the parameter, the central device 2 proceeds to a step S4. Alternatively, the central device 2 does not perform the above database manager, and the central device 2 inquires of the image file servers 1 the presence of the requested imaging data file based upon the imaging data ID. The central device 2 further determines in the step S4 whether or not a process must be performed on the requested imaging data based upon the process ID. If it is determined in the step S4 that the process ID is nil or not specified, the central device 2 proceeds to a step S9, where the first image transmission request is transmitted to the image file server 1 and terminates the current session.

On the other hand, if it is determined in the step S4 that the process ID is specified, the central device 2 retrieves a software program corresponding to the process ID from the second storage unit 23 in a step S5. Furthermore, the central device 2 generates a second image transmission request based upon the process ID and transmits to the image file server 1 the second image transmission request and the retrieved processing software in the step S5. The second image transmission request specifies that the retrieved processing software is performed on the imaging data as specified in the first image transmission request to generate second imaging data at the image file server 1. The second image transmission request further specifies that the second imaging data should be transmitted back to the terminal device 3, which has originated the first image transmission request.

Still referring to FIG. 2, at the image file server 1, it is determined in a step S25 whether or not the second image transmission request and the processing software program have been received from the central device 2. If it is determined in the step S25 that the second image transmission request and the processing software program have not been received, the preferred process proceeds to a step S26. On the other hand, if it is determined in the step S25 that the second image transmission request and the processing software program have been received, the image file server 1 retrieves the specified imaging data from the storage unit 13 according to the second image transmission request and executes the received processing software program on the retrieved imaging data to generate the second imaging data in a step S6. For example, the second image transmission request specifies a number of sets of imaging data, and the received processing software program combines the plural sets of imaging data to generate a three-dimensional image as the second imaging data.

After the execution of the processing software program is confirmed within a predetermined amount of time in a step S8, the image file server 1 transmits the second imaging data directly back to the terminal device 3 without going through the central device 2 according to the second image transmission request in a step S7 and terminates the session. After the execution of the software program is not confirmed within the predetermined amount of time in the step S8, the preferred process proceeds to a step S27, where an error message is sent to the terminal device 3 and then to the step S26. Lastly, in the step S26, it is determined whether or not the first image transmission request has been received. If it is determined in the step S26 that the first image transmission request has been received, the first imaging data is transmitted back to the terminal device 3 in a step S10, and the preferred process terminates the current session. On the other hand, if it is determined in the step S26 that the first image transmission request has not been received, the preferred process terminates the current session.

The above exemplary process of generating a three-dimensional image reduces network traffic under a certain situation. For example, assuming that the scanned imaging data over the lung area of 40 cm at a 0.5 mm slice contains 800 images and each image contains 512 K bytes of imaging data, the data size is approximately over 400 M bytes of the imaging data. The processing programs are generally relatively smaller than the above imaging data. According to the preferred process in the current invention, since the original imaging data of a voluminous size does not have to be transmitted over the network when the corresponding smaller processed imaging data is requested, the network traffic is substantially reduced. Consequently, the preferred process also substantially reduces an amount of response time in the network-based distributed medical image archiving and communication system.

In addition to the database management for the location of the imaging data files, another preferred embodiment of the central device 2 also optionally manages dynamic information on the transmission rate and the processing speed of the processing software programs at the image file server 1 and or at the central device 2. That is, in response to an image transmission request from the terminal device 3, the central device 2 refers to the information in order to optimize the processing of the image transmission request by selecting a processing software program and a transmission path in accordance with a user specified priority criterion or a set of user specified criteria. The managed information is not limited to the above mentioned information and includes other relevant information in optimizing the image transmission request from the terminal device 3. Some information such as the utilization of the CPU 13 at the image file servers 1 is dynamic while others such as the physical memory size are static over time. The information is managed in a predetermined format such as tables in one preferred embodiment.

As a result of the above described information management, in certain situations, it is more efficient to process the requested imaging data at the image file server 1, where the requested imaging data is not stored. In other words, in the certain situations, it is more efficient and or in accordance with the user priority to transmit the requested imaging data from a first image file server where the imaging data is stored to a second image file server to which the specified processing software program is transmitted from the central device 2. Thus, the requested imaging data is processed at the second image file server to generate the second imaging data before transmitting back to the requesting terminal device 3.

In an alternative embodiment of the above described system according to the current invention, the terminal devices 3 are directly connected to the central device 2 and or the image file server 1. As long as the terminal devices 3 are identified in the network 4 and are able to communicate with the central device 2 and the image file server 1 via the network I/F 31, the terminal devices 3 are connected to the network 4 in other manners.

Figure 3:
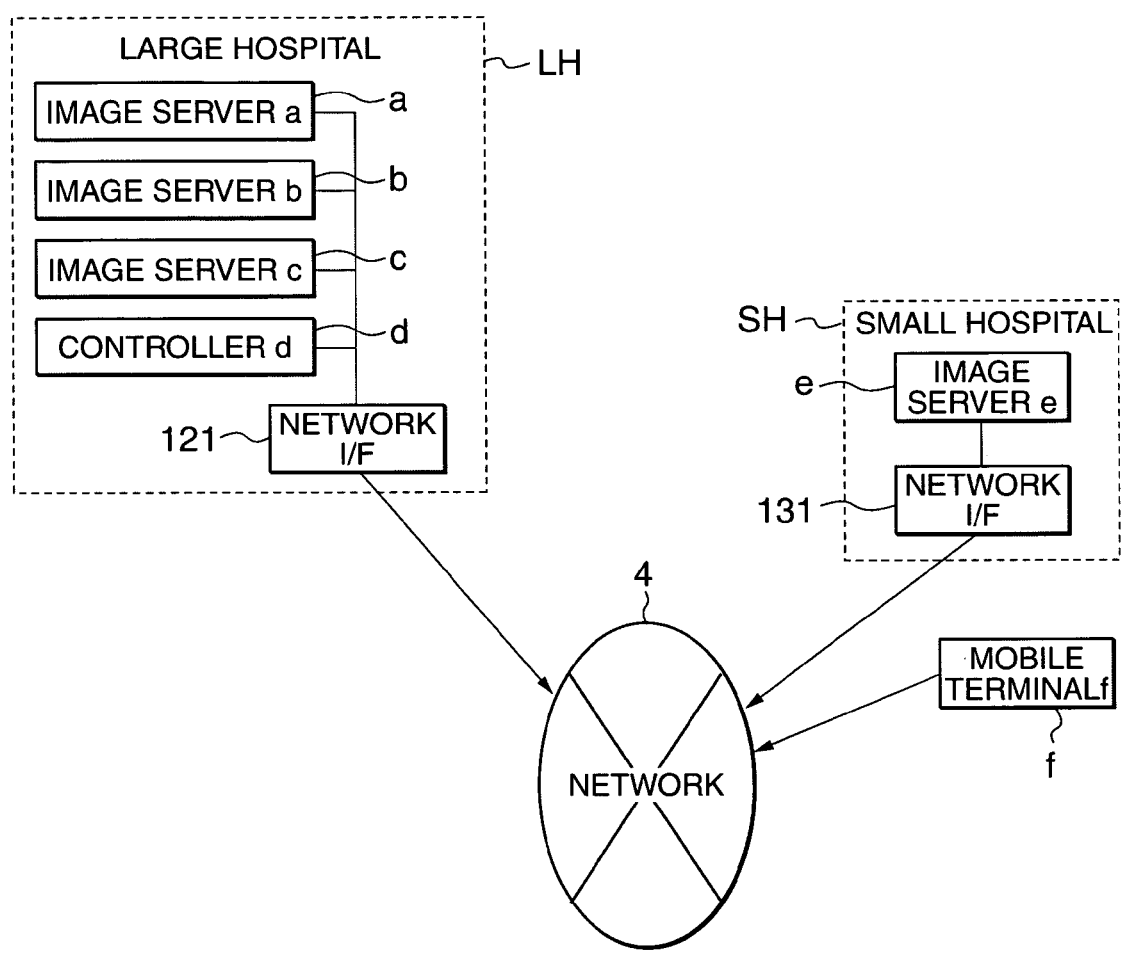
FIG. 3 is a diagram illustrating a second preferred embodiment of the system for archiving, processing and communicating medical imaging data according to the current invention.

Now referring to FIG. 3, a diagram illustrates a second preferred embodiment of the system for archiving, processing and communicating medical imaging data according to the current invention. The system includes a first or large server system LH at a large hospital, a second or small server system SH at a smaller hospital or an affiliated clinic, a mobile terminal f for accessing the second server system SH and a network 4 such as a local network (LAN), an intra network and or the Internet that connects the above file server systems LH, SH and the terminal f. The first server system LH further includes a first image file server a, a second image file server b, a third image file server c, a first controller or control unit d for controlling the image file servers a, b, c and a network interface (I/F) 121 for connecting to the network 4. The image file servers a, b and c store a large amount of X-ray, CT, ultrasound or MRI imaging data that has been collected at the large hospital or other hospitals including the small hospital. The stored imaging data is associated with a patient name, a scanned date and time, a modality or scanning device and other relevant information. The image file servers a, b and c include any combination of magnetic, optical and magneto-optical storage media. Although not illustrated, the first file server system LH is connected to a CT scanner that generates scanned imaging data to be stored at the image file server a, b or c. The control unit d and the image file servers a, b and c each include a general purpose computer with a CPU, a ROM, a RAM, a magnetic storage, an input device such as a keyboard and or a mouse as well as a display.

The first control unit d executes instructions to write and read imaging data to and from the image file servers a, b and c to function as a database manager. The first control unit d also executes instructions to receive the imaging data for storage from the second server system SH via the network 4 and the network I/F 121. The first control unit d also communicates with the image file servers a, b and c to inquire about the existence of specified imaging data as well as the load status of the CPU. The first control unit d further selects one of the image file servers a, b and c based upon predetermined criteria or a user priority to execute a certain processing program on the specified imaging data at the selected one of the image file servers a, b and c. Lastly, the first control unit d transmits the processed imaging data to the network 4 via the network I/F 121 and or stores the processed imaging data back in the image file server a, b or c.

Still referring to FIG. 3, the small server system SH further includes an image file server e for performing a certain specified process and a second network interface (I/F) unit 131 for interfacing the small server system SH with the network 4. The image file server e includes a general-purpose computer with a CPU, a ROM, a RAM, a magnetic storage, an input device such as a keyboard and or a mouse as well as a display. The image file server e functions to communicate with the mobile terminal f and the large server system LH. The image file server e executes instructions to write and read information to and from its own memory storage unit. The information includes at least a part of the imaging data that is stored at the image file servers a, b and c. The information also includes a patient name, a scanned date/time, a modality or scanning device and other relevant information that are associated with the stored imaging data in the image file servers a, b and c. The memory storage in the image file server e includes any combination of magnetic, optical and magneto-optical storage media.

Lastly, with respect to FIG. 3, the mobile terminal f further includes a CPU, a ROM, a RAM, a magnetic storage, an input device such as a keyboard and or a mouse, a display and a network interface for interfacing the mobile terminal f with the network 4. The mobile terminal f is connected to the network 4 either wirelessly or by a certain line. The mobile terminal f functions as a terminal device that a user utilizes to view the medical image that is stored at the image file server e at the small server system SH via the network 4. To do so, the user selects a certain imaging data from the mobile terminal f. In addition, the user specifies a certain process to be performed on the selected imaging data. The mobile terminal f stores certain predetermined software programs to process the selected imaging data at the mobile terminal f. In other words, the CPU in the mobile terminal f is sufficiently powerful enough to locally perform a selected one of the processing software programs on the imaging data that is received from the image file server e. One exemplary software program processes the imaging data to generate an input in a predetermined format to the CAD from the image data. Other exemplary software programs generate a three-dimensional image, a combined image of selected portions and chronologically arranged images of a certain portion. However, under certain conditions or based upon user specified criteria, the mobile terminal f determines that the selected process is externally processed. In case of the external processing, the CPU in the mobile terminal f executes instructions to transmit to the control unit d via the network 4 the processing software program for the selected process if the processing software program does not exist at the small server system SH. Although the diagram illustrates a single one of the large server system LH, the small server system SM and the mobile terminal f, a plurality of the large server systems LH, the small server systems SM and or the mobile terminals f is connected to the network 4.

Figure 4:
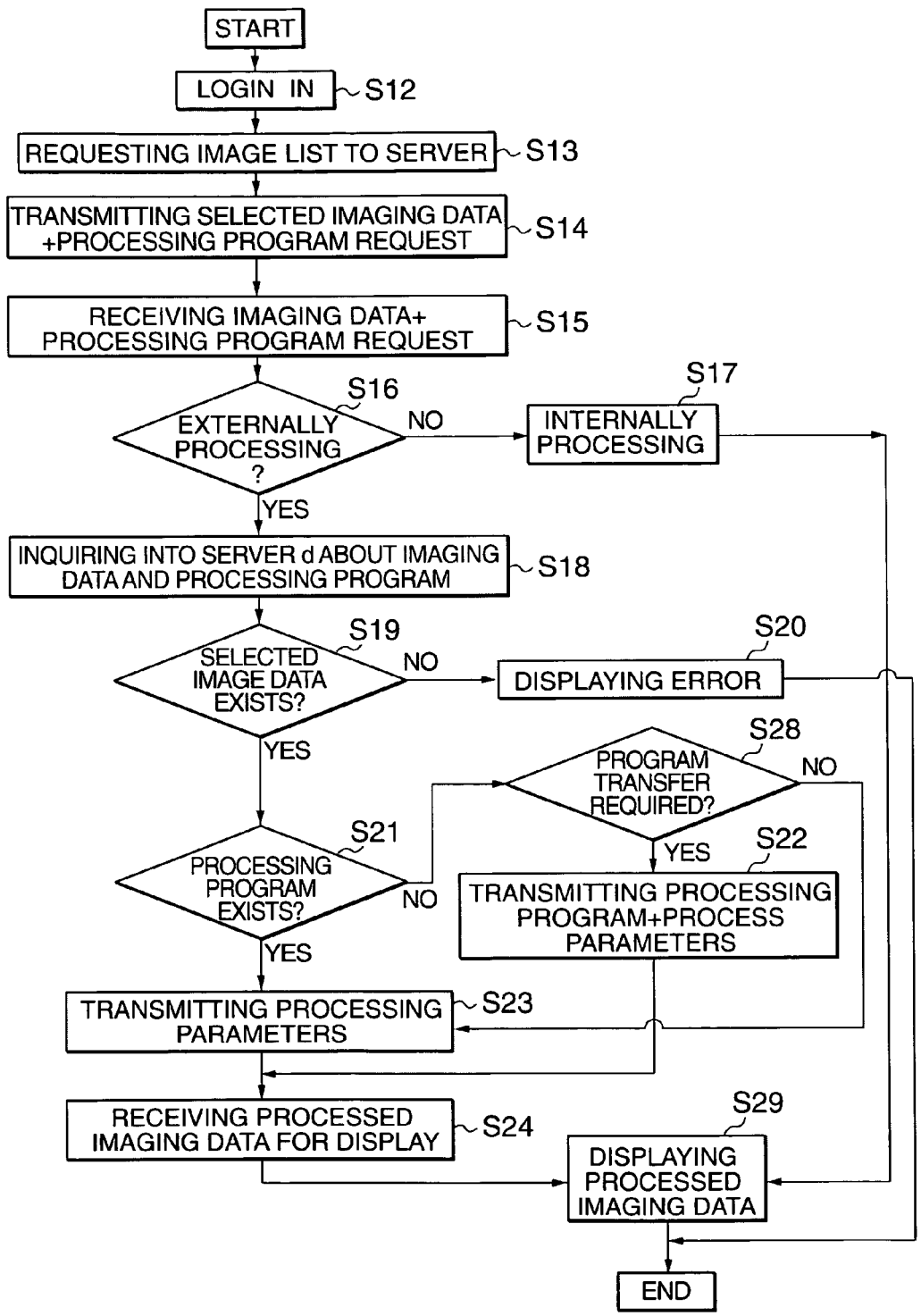
FIG. 4 is a flow chart illustrating steps involved in a second preferred process of archiving, processing and communicating the imaging data according to the current invention.

Now referring to FIG. 4, a flow chart illustrates steps involved in a second preferred process of archiving, processing and communicating the imaging data according to the current invention. To describe the second preferred process, although the units or components of FIG. 3 are referred, the second preferred process of FIG. 4 is not limited to these units or components of FIG. 3. In a step S12, a user logs in the image file server e at the small server system SH from the mobile terminal f via the network by specifying a user ID and a password. After a successful log in, the user requests from the mobile terminal f a list of the images or an image list in a step S13. The request is optionally limited to a combination of a patient name, a scanning date, an attending doctor and other relevant information. In response to the image list request, the image file server e selects a list of matching information and transmits the selected image list to the mobile terminal f in a step S14. The mobile terminal f displays the image list transmitted from the image file server e, and the user selects a particular image. When a series of images or a three-dimensional image is desired, a first image or a representative image is selected to save an amount of imaging data to be transmitted over the network. The mobile terminal f requests the selected image to the image file server e in the S14. In response to the selected image request, the image file server e transmits the selected imaging data back to the mobile terminal f, and the mobile terminal f displays the transmitted image in a step S115.

In the step S15, the mobile terminal f also displays icons that represent a special processing. Three-dimensional processing includes surface rendering and volume rendering while non-three dimensional processing includes maximum intensity planar, a step conversion process, an edge enhancement process and computer aided diagnosis (CAD). CAD processes the imaging data to detect an abnormal portion in the image. Assuming that the user selects one of the icons and inputs the corresponding parameters, it is determined whether or not the selected process is performed at an external device or outside of the mobile terminal f in a step S16. For example, the above defined three-dimensional processing is externally performed in the second preferred process. If it is determined in the step S16 that the requested process is not externally processed or internally processed at the mobile terminal f, the CPU of the mobile terminal f executes the specified processing program that is stored in the mobile terminal f in a step S17. The mobile terminal f displays the processed imaging data at its own display in a step S29. Thus, the second preferred process ends the current session.

Still referring to FIG. 4, in case it is determined in the step S116 that the requested process is externally processed outside the mobile terminal f, the mobile terminal f inquires of the control unit d if the corresponding image and the selected software program exist in the server system LH in a step S18. The control unit d transmits a reply message to the mobile terminal f. If the corresponding imaging data does not exit in the image file server a, b or c according to the reply message in a step S19, the mobile terminal f displays an error message in a step S20, and the preferred process terminates the current session. On the other hand, if in the step S19 it is determined that the corresponding imaging data exits in the image file server a, b or c, but that the selected software does not exit in the server system LH in a step S21, it is further determined in a step S28 as to whether or not the processing software program needs to be transferred. If it is determined in the step S28 that the processing software program does not need to be transferred, the preferred process proceeds to a step S23. On the other hand, if it is determined in the step S28 that the processing software program needs to be transmitted, the mobile terminal f transmits the selected software and the associated processing parameters to the control unit d over the network 4 in a step S22, and the preferred process proceeds to a step S24. Lastly, if it is determined in the step S21 that the selected software exits in the server system LH, only the associated processing parameters are sent to the control unit d in a step S23. After the control unit d performs the specified process on the selected imaging data in the server system LH, the control unit d transmits the processed imaging data with a special ID to the mobile terminal f. The mobile terminal f receives the processed imaging data in a step S24 and displays the processed imaging data in a step S29 if the special ID confirms the requested image. Thus, the second preferred process ends the current session.

Figure 5:
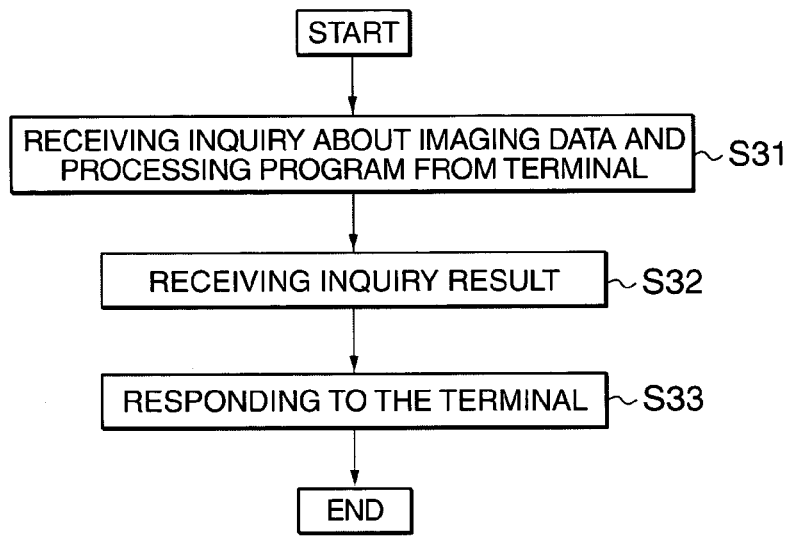
FIG. 5 is a flow chart illustrating a set of steps at the control unit in the second preferred process of archiving, processing and communicating the imaging data according to the current invention.

Now referring to FIG. 5, a flow chart illustrates a set of steps at the control unit d in the second preferred process of archiving, processing and communicating the imaging data according to the current invention. The following steps are performed when the mobile terminal f makes an inquiry to the control unit d on the existence of the imaging data and the processing software program in the step S118 of FIG. 4. In response to the inquiry from the mobile terminal f, the control unit d receives the information on the imaging data and the processing software in a step S31. The control unit d inquires of the image file servers a, b and c whether or not the imaging data and or the processing software exist in a step S32. The control unit d then transmits a reply from the image file servers a, b and c to the mobile terminal f in a step S33 and terminates the session.

Figure 6:
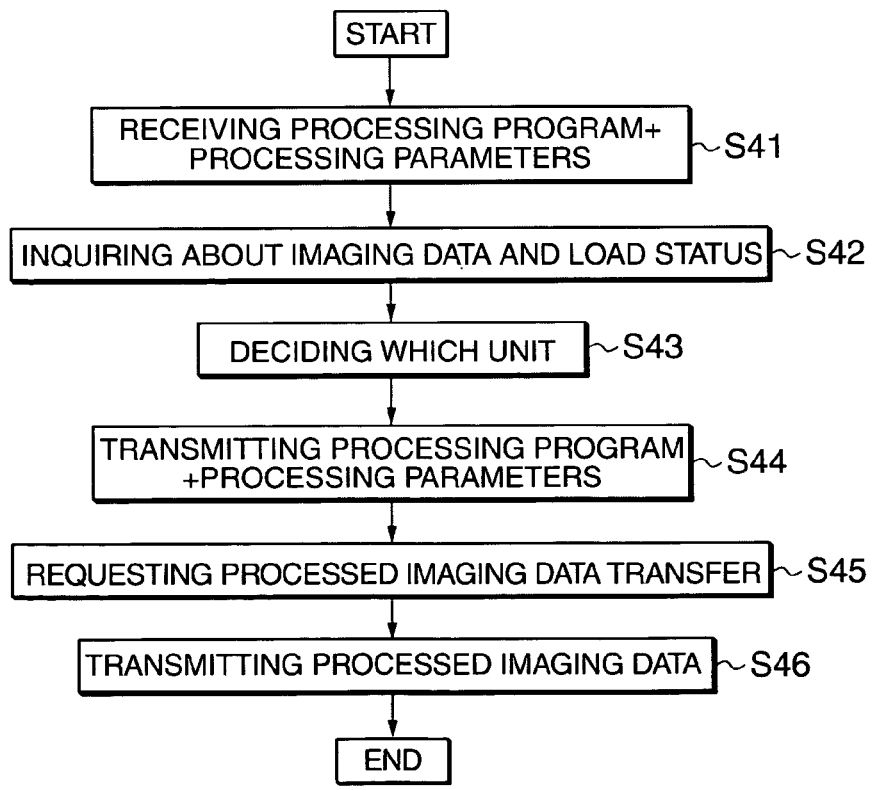
FIG. 6 is a flow chart illustrating another set of steps at the control unit in the second preferred process of archiving, processing and communicating the imaging data according to the current invention.

FIG. 6 is a flow chart illustrating another set of steps at the control unit d in the second preferred process of archiving, processing and communicating the imaging data according to the current invention. The following steps are performed when the mobile terminal f transmits to the control unit d the processing software program and the associated parameters in the step S22 of FIG. 4. After receiving the information on the specified process parameters and the selected software program from the mobile terminal f in a step S41, the control unit d inquires of the image file servers a, b and c whether or not the specified imaging data and the selected software program exist in a step S42. Assuming that one of the image file servers a, b and c rather than the control unit d processes the imaging data, the control unit d also inquires of the image file servers a, b and c as to the current utilization level or processing load in the step S42. Based upon the response from the image file servers a, b and c, the control unit d determines which image file server is utilized in a step S43. In a step S44, the control unit d transmits the software program and or the parameter to the selected one of the image file servers a, b and c. If it is necessary, the imaging data to be processed is transmitted to the selected one of the image file servers a, b and c in a step S45. After the successful process at the selected one of the image file servers a, b and c in the step S45, the control unit d receives the processed imaging data and transmits it to the mobile terminal f in a step S46.

Figure 7:
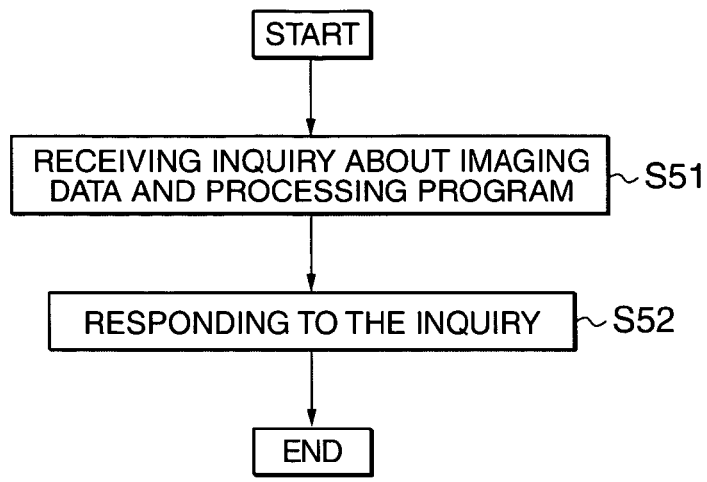
FIG. 7 is a flow chart illustrating a set of steps at the image file server in the second preferred process of archiving, processing and communicating the imaging data according to the current invention.

FIG. 7 is a flow chart illustrating a set of steps at the image file server a, b or c in the second preferred process of archiving, processing and communicating the imaging data according to the current invention. The following steps are performed when the control unit d makes an inquiry to the image file servers a, b and c on the existence of the imaging data and the process software program in the step S32 of FIG. 5. After receiving the inquiry from the control unit d in a step S51, each of the image file servers a, b and c performs the inquiry and responds to the control unit d in a step S52. The response includes the existence or the absence of the specified imaging data and processing software program.

Figure 8:
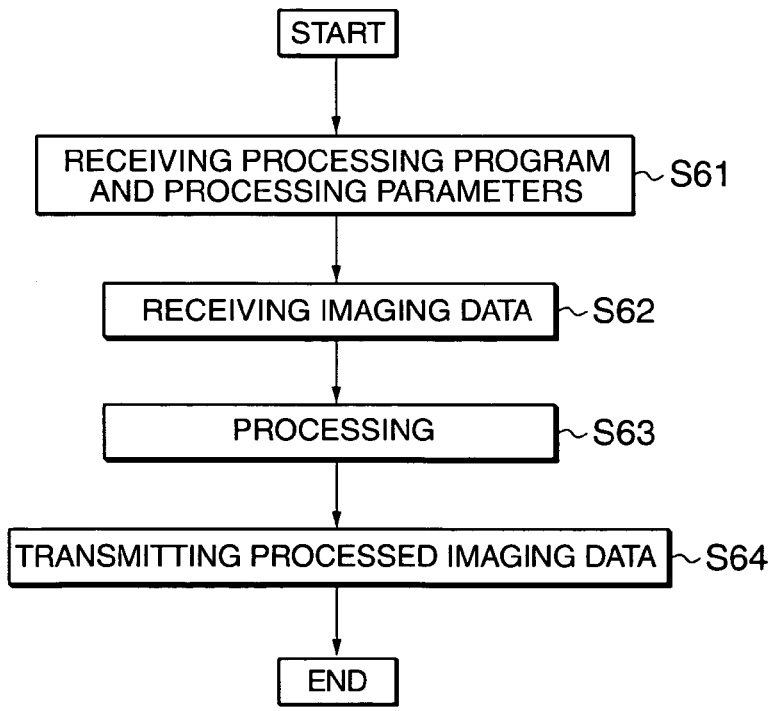
FIG. 8 is a flow chart illustrating another set of steps at the image file server in the second preferred process of archiving, processing and communicating the imaging data according to the current invention.

FIG. 8 is a flow chart illustrating another set of steps at the image file server a, b or c in the second preferred process of archiving, processing and communicating the imaging data according to the current invention. The following steps are performed when the specified program is to be externally executed at a selected one or ones of the image file servers a, b and c as initiated in the step S44 of FIG. 6. In the following steps, it is assumed that the control unit d has determined that the imaging data and or the processing software program need to be transmitted among the image file servers a, b and c. Alternatively, it is assumed that the control unit d has received the imaging data and or the processing software program to be transferred to the selected one of the image file servers a, b and c. After receiving the processing parameters and the processing software program in a step S61, the selected one or ones of the image file servers a, b and c also receives the imaging data in a step S62. Subsequently, the selected one or ones of the image file servers a, b and c executes the software program on the imaging data according to the processing parameters in a step S63 and transmits the processed imaging data back to the control unit d in a step S64.

As described with respect to FIGS. 3 through 8, the second preferred embodiment and process enable the PACS to archive, process and communicate the imaging data in a flexible manner. The flexibility optimizes the efficiency for the user-specified post-scanning process on the imaging data by utilizing the best available resources in the system. Other aspects of the above described optimization are further described in the following preferred processes.

Figure 9:
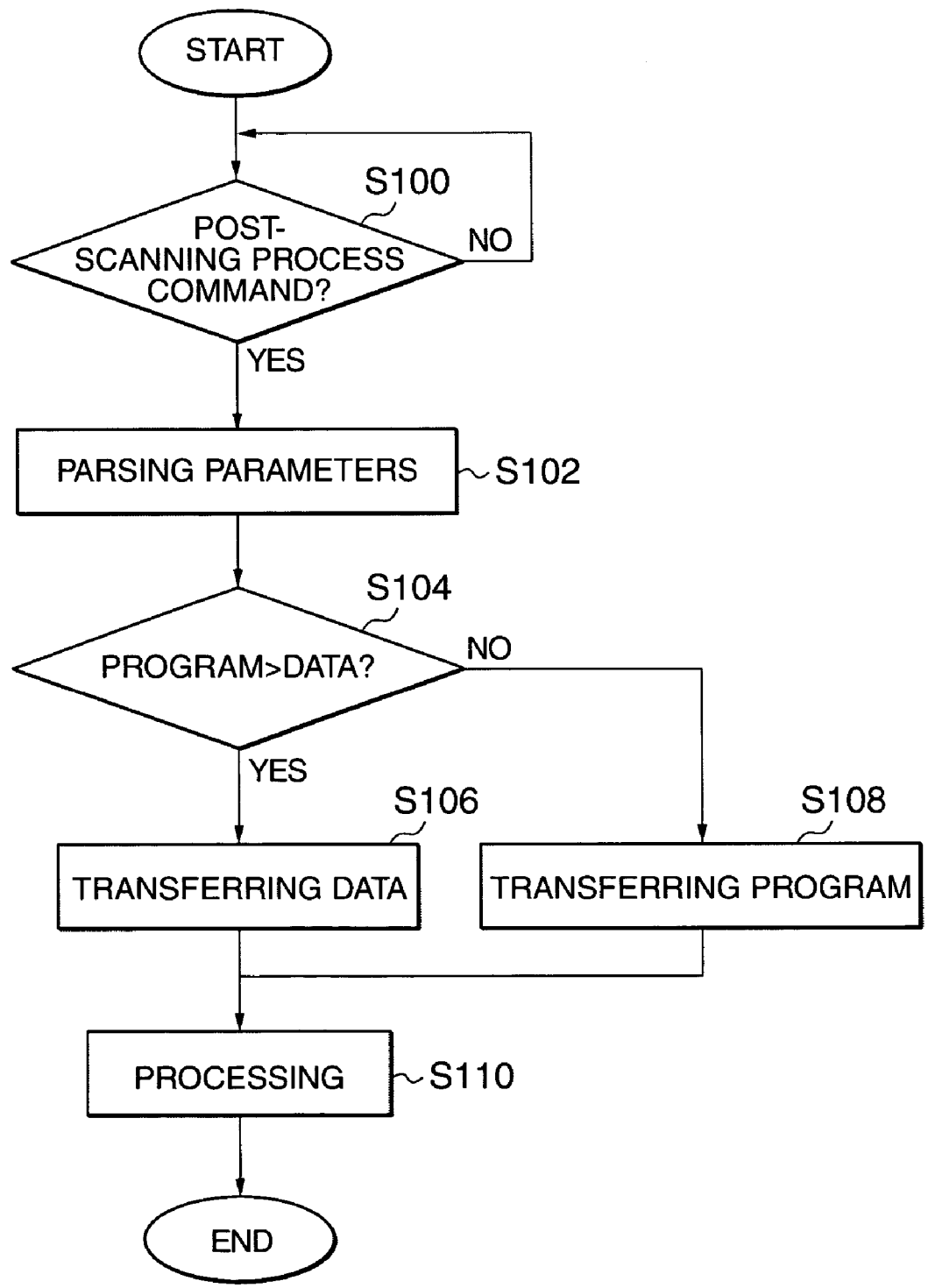
FIG. 9 is a flow chart illustrating general steps involved in a third preferred process of archiving, processing and communicating the imaging data according to the current invention.

Now referring to FIG. 9, a flow chart illustrates general steps involved in a third preferred process of archiving, processing and communicating the imaging data according to the current invention. The following steps will be described in general rather than referring to the specific elements or units of the first and second preferred embodiments in FIG. 1 or 3 since the third preferred process is implemented by either of the first and second preferred embodiments or other relevant systems. In a step S100, it is determined whether or not a post-scanning process command is issued by an authorized user who has been logged in the system according to the current invention. If the post-scanning process command has not been issued in the step S100, the third preferred process waits for one. On the other hand, if the post-scanning process command has been issued in the step S100, the post-scanning process command is parsed in a step S102. It is assumed that the post-scanning process command includes a command ID, an imaging data ID and processing parameters that are associated with the command ID. The command ID specifies a particular processing software program or a group of processing software programs that are stored at a know location which is associated with the command ID. The imaging data ID specifies a particular piece of imaging data or a set of imaging data that is stored at a know location which is associated with the imaging data ID. The processing parameters are a set of values indicative of a certain mode or manner that the specified processing software is executed.

Still referring to FIG. 9, based upon the parsed parameters in the step S102, the file size of the imaging data is compared to the file size of the specified software program in a step S104. The file size of the imaging data and the specified software program is obtained from a certain memory location or table before the actual imaging data and software program files are accessed. For example, a table contains information including the file size of the imaging data files and the software program files, and the table location is known to the system. Assume that the software program as specified in the post-scanning command exists at a first device that is connected to the common network, but is different from a second device which contains the imaging data to be processed. Also assume that the first and second devices are independently capable of executing the software program to process the imaging data. Based upon the comparison in the step S104, if it is determined whether or not the software program file size is larger than the imaging data file size. If it is determined in the step S104 that the program file is larger than the imaging data file, the imaging data is transferred to the device that contains the software program in a step S106. On the other hand, if it is determined in the step S104 that the program file is not larger than the imaging data file, the software program is transferred to the device that contains the imaging data in a step S108. Lastly, the software program is run to perform a post-scanning process on the imaging data in a step S110. Based upon the comparison result in the step S104, the least amount of the information is transferred over the network either in the step S106 or S108 before processing the image data in the step S110 in the third preferred process.

Figure 10:
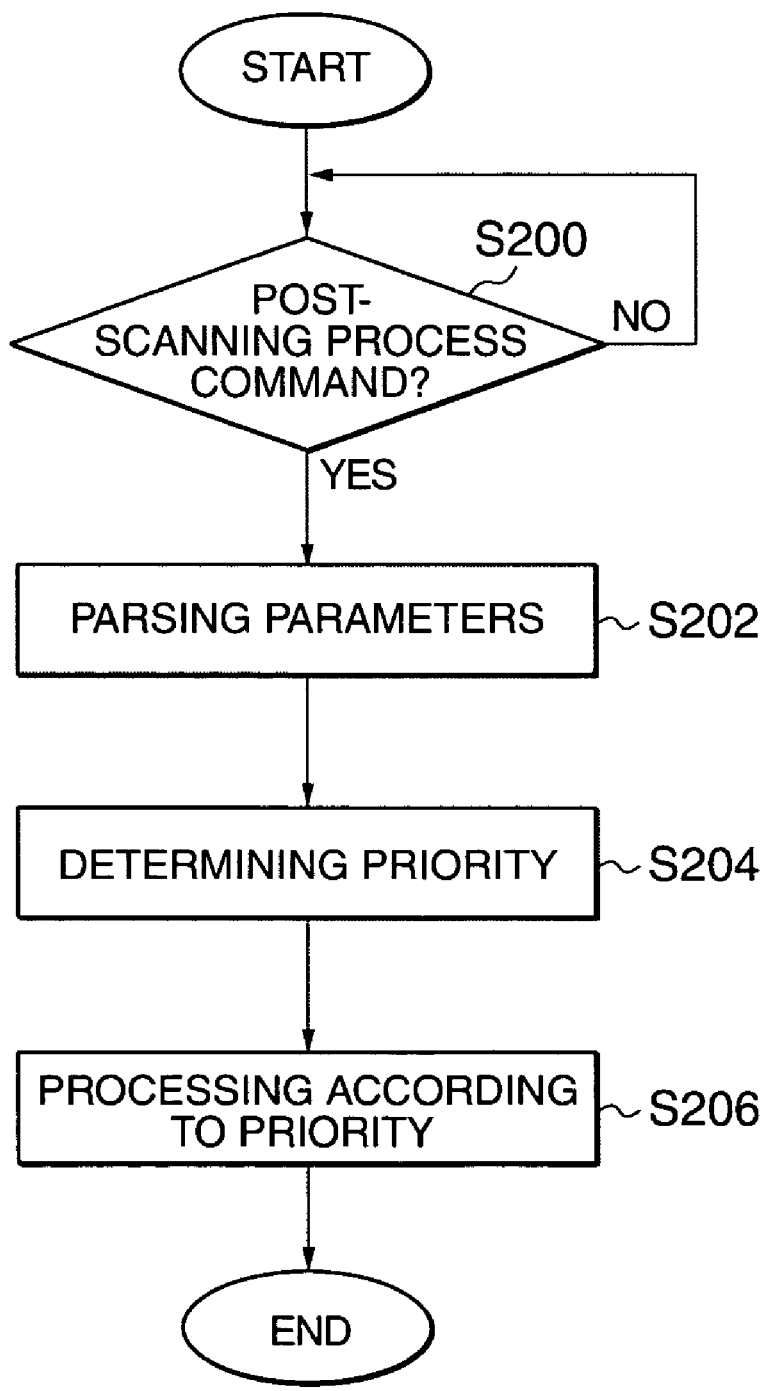
FIG. 10 is a flow chart illustrating general steps involved in a fourth preferred process of archiving, processing and communicating the imaging data according to the current invention.

Now referring to FIG. 10, a flow chart illustrates general steps involved in a fourth preferred process of archiving, processing and communicating the imaging data according to the current invention. The following steps will be described in general rather than referring to the specific elements or units of the first and second preferred embodiments in FIG. 1 or 3 since the fourth preferred process is implemented by either of the first and second preferred embodiments or other relevant systems. In a step S200, it is determined whether or not a post-scanning process command is issued by an authorized user who has been logged in the system according to the current invention. If the post-scanning process command has not been issued in the step S200, the fourth preferred process waits for one. On the other hand, if the post-scanning process command has been issued in the step S200, the post-scanning process command is parsed in a step S202. It is assumed that the post-scanning process command includes a command ID, an imaging data ID and processing parameters that are associated with the command ID. The command ID specifies a particular processing software program or a group of processing software programs that are stored at a know location which is associated with the command ID. The imaging data ID specifies a particular piece of imaging data or a set of imaging data that is stored at a know location which is associated with the imaging data ID. The processing parameters are a set of values indicative of a certain mode or manner that the specified processing software is executed.

Still referring to FIG. 10, based upon the parsed parameters in the step S202, a priority or processing criteria is determined in a step S204. The priority or processing criteria is a set of values that a user has specified in the processing parameters to indicate a manner in which the specified processing software program should be executed. For example, the user specifies that the post-scanning command to be executed and completed within the shortest amount of time. This priority means that the user wants to receive the computed result as soon as possible regardless of the costs associated with the execution of the processing software program. Another example is that the user specifies that the post-scanning command to be executed and completed at the least expensive manner. This priority means that assuming the use of the various network resources such as the use of the CPU time is charged to the user, the user wants to incur the least amount of the cost associated with the execution of the specified post-scanning process. Yet another example is that the user specifies that the post-scanning command to be executed and completed with the least amount of network traffic. This priority means that the network traffic amount that is associated with the program execution is the least so that the network is least negatively affected. The above described priorities are merely illustrative and not exhaustive for practicing the current invention. Lastly, the fourth preferred process performs the process of the specified software program on the particular imaging data in a step S206 according to the priority determination result in the step S204. A certain combination of the above priorities is used in the fourth preferred process.

Figure 11:
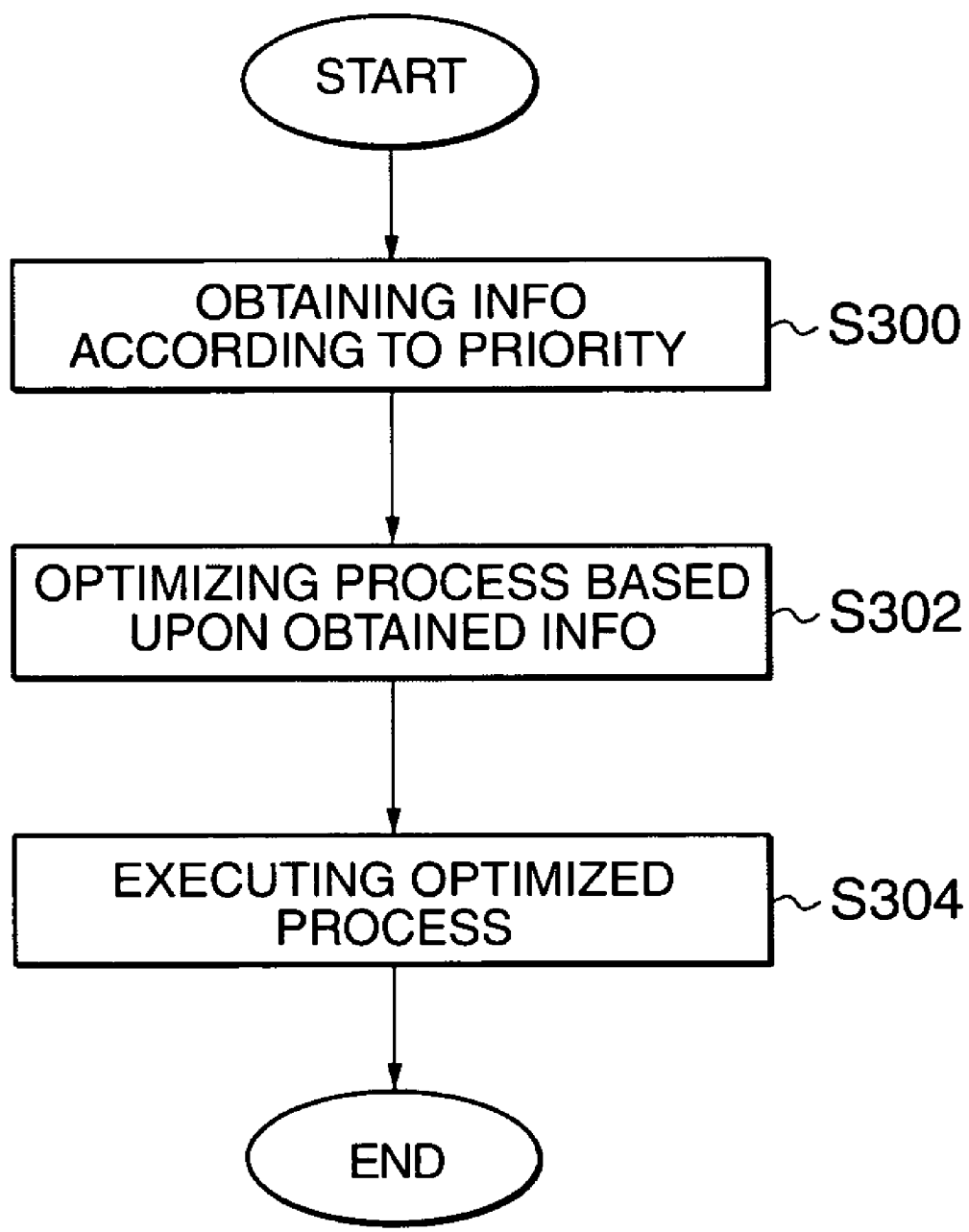
FIG. 11 is a flow chart illustrating further steps involved in the processing step of FIG. 10 in the fourth preferred process of archiving, processing and communicating the imaging data according to the current invention.

Now referring to FIG. 11, a flow chart illustrates further steps involved in the processing step S206 of FIG. 10 in the fourth preferred process of archiving, processing and communicating the imaging data according to the current invention. In a step S300, relevant information is gathered according to the user specified priority that has been determined in the step S204 of FIG. 10. For example, the user specifies that the post-scanning command to be executed and completed within the shortest amount of time. Initially, based upon the imaging data ID, the file size of the specified imaging data is determined. As will be later shown, for all existing imaging data, a predetermined set of information including the data file size is centrally maintained at a predetermined location in a certain format such as a table. Thus, the file size or the data size is obtained without actually locating the imaging data itself. Similarly, for all predetermined post-scanning process commands, a predetermined set of information is also centrally maintained at a predetermined location in a certain format such a table. The information includes the identification of various software programs that perform the substantially identical process which is identified by the command ID. The information also includes the corresponding execution rate or time for the various software programs. If the execution rate is non-linear with respect to the imaging data amount, the execution rate is noted for a predetermined range of data amounts.

The imaging data file size and the processing execution rate are relatively static information that does not change in a frequent manner. Once the information is stored at a predetermined location, the values do not change over a relatively short period of time such as a program execution period. In comparison to the above relatively static information, certain other information is more dynamic. For example, the transmission rates among the devices change more rapidly and frequently depending upon the network traffic. If the information transmission rates among the devices are centrally kept in a table, the transmission rates are updated in the table as necessary.

In the alternative to the above described information collection step 300, the relevant information is gathered on-the-fly. In stead of storing the relevant information in advance in a predetermined format such as a table, an alternative implementation of the information collection step 300 is to make relevant inquiries to the database managers or the utilization managers to gather the information according to the user-specified priority. For example, if the user specifies the shortest execution for the priority, a series of inquiries is made to the utilization managers for gathering the current transmission rates among the devices. The on-demand information gathering is efficient for certain information such as the transmission rate. Although the relatively static information such as the execution rate and the file size may be also gathered in the on-demand by sending inquiries to the relevant database managers for managing the imaging data files and the processing software programs, the frequent inquiries over the network increase unnecessary traffic and cause some undesirable effects.

Still referring to FIG. 11, based upon the above gathered information, optimization is performed in a step S302. If the priority is to minimize the execution time as described with respect to the step 300, one aspect of time optimization is accomplished in the step S302 by selecting the software program identification of the associated software program having the fastest execution rate for the data size of the specified imaging data. Another aspect of time optimization is accomplished also in the step S302 by minimizing the transmission time for transmitting the selected software program and or the selected imaging data over the network during the process. Based upon the identification of the selected software program and imaging data, the location is identified. If it is necessary to transmit the selected software program and or imaging data over the network, the transmission path is selected among available paths for minimizing the transmission time. Similarly, after the imaging data is processed, if the processed imaging data needs to be transmitted over the network to a destination as specified in the processing parameters, the delivery transmission path is also selected to minimize the transmission time. The time from all aspects of the post-scanning command execution is totaled in order to determine the optimized process sub-steps.

Lastly, in a step S304, the above described optimized process is performed based upon the selected information of the step S302 according to the user-specified priority. As described above for the example of the shortest execution time, the sub-steps have been selected in the step S302. For example, if it has been determined in the step S302 that the shortest command execution time is accomplished by executing a Nth software program that is associated with the same command ID, the step S304 executes the Nth software program to process the specified imaging data. The exception to executing the already selected sub-steps includes certain situations where the already selected sub-steps fail to provide an optimized process. For example, if there is a substantial time lag between the steps 302 and 304, the transmission rate for the selected transmission path has been substantially changed. In these similar situations, the optimization step 302 is repeated if the user-specified priority is better served.

Figure 12:
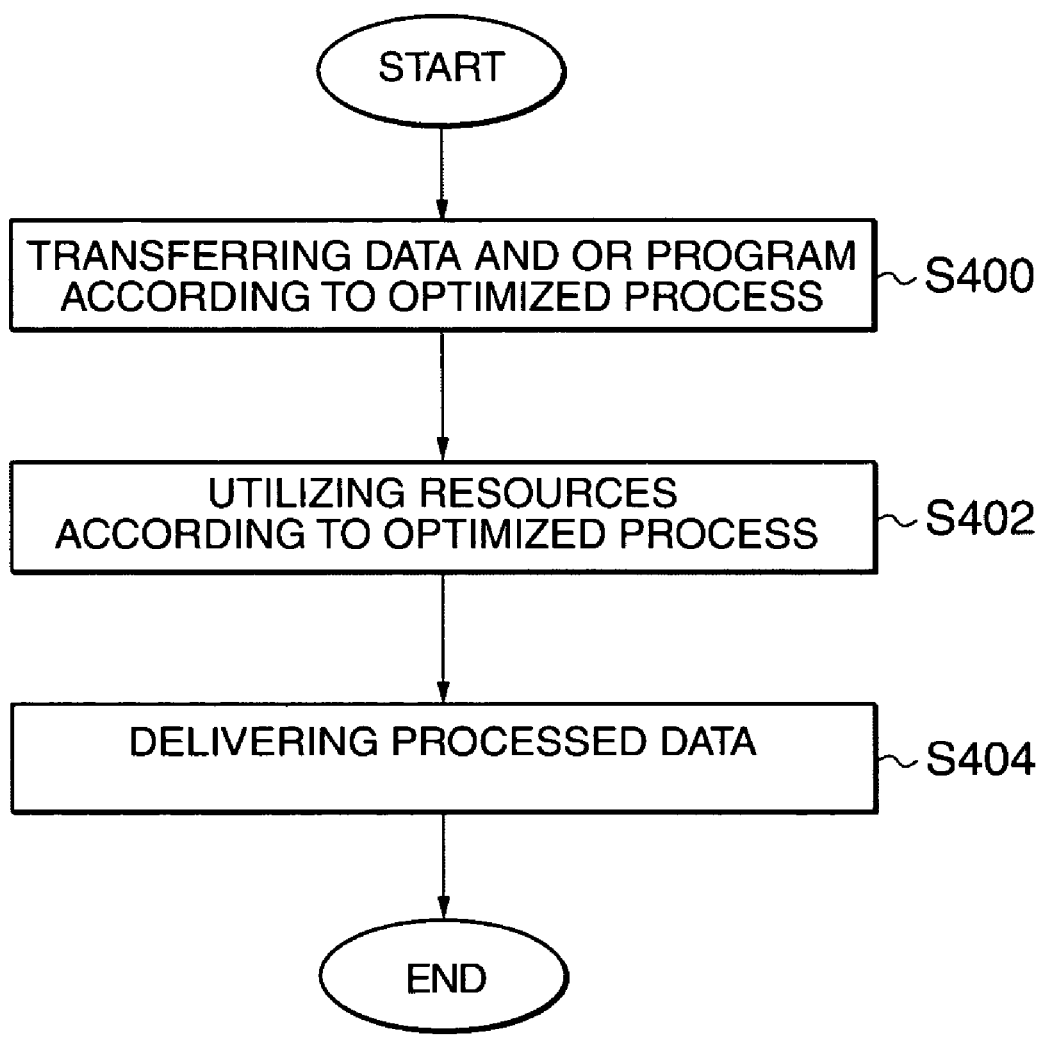
FIG. 12 is a flow chart illustrating further steps involved in the execution step of FIG. 11 in the fourth preferred process of archiving, processing and communicating the imaging data according to the current invention.

Now referring to FIG. 12, a flow chart illustrates further steps involved in the execution step S304 of FIG. 11 in the fourth preferred process of archiving, processing and communicating the imaging data according to the current invention. In general, as described above, the execution step follows what has been already determined. In a step S400, a file transfer takes place if it has been already determined that the selected imaging data and or the software program is to be transmitted over the network between the devices. After the completion of the file transfer of the selected imaging data and or the software program in the step S400, the software program is executed in a memory by a selected central processing unit (CPU) and or a selected display processing unit (DPU) in a step 402. After the processed imaging data has been generated in the step S402, the processed imaging data is delivered to a destination as specified in the processing parameters over the already selected transmission path in a step S404. The sub-steps S400, S402 and S404 are merely exemplary and not exhaustive for the execution step S304.

Referring to FIG. 13, an exemplary table illustrates information in a predetermined table format to be used in the above preferred processes according to the current invention. It is assumed that Table 1 contains execution time by a predetermined processor A that is available in the network. In determining the execution time, it is also assumed that the processor A is dedicated or fully available to execute a specified processing software program. Table 1 contains information on approximate execution time for each of the processing software programs for processing data of a known size. For example, it takes 0.15 milliseconds for Processor A to execute the instructions of Program B to process 512 kilobytes of the data if the Processor A is filly dedicated. In reality, if similar tables are available for other processors that are available on the same network, the above assumed execution time is not realistic for selecting a processor according to a priority indicative of the shortest execution time if the Processors A through C are shared as a network resource and no processor is dedicated to a specified task. On the other hand, given an imaging data size, Table 1 is useful in selecting the fastest processing program for Processor A. Furthermore, given a processing software program, Table 1 is useful in determining an optimal imaging data size to be processed by the Processor A. Since the information in Table 1 is relatively static, the information is not updated on a frequent basis.

Referring to FIG. 14, an exemplary table illustrates information in a predetermined table format to be used in the above preferred processes according to the current invention. Table 2 contains information on imaging data files at a file server A. The information includes an imaging data ID, a corresponding data size or file size, a scanned date, a physical memory file location or the network file location and so on. The information in Table 2 is used in a variety of ways by the system for archiving, processing and communicating the imaging data according to the current invention. For example, to determine an amount of data to be transferred for the imaging data ID=1, the data size in Table 2 is referred to obtain 400 mega bytes. Although the information in Table 2 is also relatively static, the information may be updated on an occasional basis. For example, the imaging data location may be changed over time.

The above described Table 1 and Table 2 are stored at a predetermined network location as a part of the system for archiving, processing and communicating the imaging data according to the current invention. In one preferred embodiment, the table contents are accessed and maintained through a database manager. In another preferred embodiment, the table contents are directly accessed by reading the particular memory location with a certain predetermined offset value. In any case, the tables are one form of the central information management that can be implemented in other ways according to the current invention.

With respect to FIGS. 15 through 20, the following tables 3 through 8 are used to illustrate the further details of certain steps in the above preferred process as described with respect to FIGS. 5 and 6 according to the current invention. As shown in Table 3, as the control unit d receives the information on the processing software in the step S41 of FIG. 6, the information includes the file size of the processing software program as well as the processing speed of the processing software. The processing software size is obtained from Table 3 as shown in FIG. 15. Table 3 also includes additional information on the processing description and the standard processing time. The standard processing time is defined as an amount of time in seconds to process a predetermined size of the standard imaging data such as 10 Mega bytes (MB) when a predetermined CPU is dedicated 100% to process the known imaging data using a given processing software program as identified by the program ID. Thus, the received information in the step S41 includes the standard processing time for the processing software program. For the following description of the illustrative steps, it is assumed that the imaging data has data ID of D whose data size is 300 MB while the program ID is 2 for "3D_MPR" whose program size is 10 MB and the standard processing time is 30 seconds.

Now referring to FIG. 16, based upon the static information such as file location and the dynamic information such as the CPU utilization, the server information is generated as shown in Table 4. In the step S42 of FIG. 6, the control unit d inquires of the image file servers a, b, c and e the load or the CPU utilization in percent and the file size of the specified imaging data. The imaging data size is obtained from Table 2 as shown in FIG. 14. In the step S42, the control unit d also inquires of the image file servers a, b, c and e as to whether or not the specified imaging data and the selected software program exist. Table 4 also includes the entry for the mobile terminal f. In addition to the above described information, the control unit d also receives the following information. In this example, Table 4 shows that the specified imaging data D exists at the image servers b and e while the processing software program 2 exists at the image file server a and the mobile terminal f. The CPU utilization is the highest at the image file server a and c; and the lowest at the mobile terminal f.

Now referring to FIGS. 17 and 18, additional static and dynamic information is received at the control unit d. Table 5 shows static information such as a relative CPU performance level and a memory size among the image file servers a, b, c and e and the mobile terminal f. Assuming that the image file servers a and e have the same performance level that is represented by a value 100, a higher performance level is indicated by more than 100 while a lower performance level is indicated by less than 100. The memory size is shown in MB. Table 6 shows dynamic information such as a transmission rate in mega bits per second (Mbps) in various segments of the network. The segments for various transmission rates include a transmission rate within the large hospital (LH), between the large hospital and the small hospital (LH-SH), within the small hospital (SH), between the large hospital and the mobile terminal (LH-M) and between the small hospital and the mobile terminal (SH-M). The above transmission rates change over time.

Now referring to FIG. 19, based upon the information in Tables 4, 5 and 6, the following transmission time is estimated as shown in Table 7 according to the current invention. For each of the segments as described with respect to Table 6, the imaging data transmission time, the program transmission time and the processed imaging data transmission time. The imaging data transmission time is defined by following formula.

The imaging data size (MB)/(transmission rate (Mbps)/8)

Similarly, the program data transmission time is defined by following formula.

The processing software program size (MB)/(transmission rate (Mbps)/8)

Lastly, the image processing time is defined by following formula.

The standard processing time×(processed imaging data size/standard imaging data size)/{(1−CPU utilization rate)×relative CPU performance level}

To calculate the above various transmission times, it is assumed that the imaging data size is the same as the standard imaging data size. It is further assumed that the processed imaging data size is 5 MB.

Now referring to FIG. 20, a turn around time or a total response time at each processing entity is calculated to execute the program ID=2 or "3D_MPR" on the imaging data ID=D based upon the information in Tables 3 through 7. For each of the image file servers a, b, c and e and the mobile terminal f, Table 8 shows the imaging data transmission time, the software program transmission time, the CPU processing time for the image process, the processed imaging data transmission time and the total response time which includes the above four amounts of time. Among the above processing entities, the image file server c has the least amount of total response time or 36.48 seconds. Thus, the control unit d in the step S43 of FIG. 6 decides that the image file server c performs the processing task based upon the least total response time.

As shown in Table 4, the image file server c stores neither the imaging data D nor the processing software program 2. In order for the image file server c to proceed, the control unit d transmits a command to transfer the imaging data D from the image file sever b to the image file server c. Although the imaging data D exists at the image file servers b and e, the image file server b has been selected because of the shorter transmission time from the image file server b to the image file server c. Similarly, the control unit d transmits a command to transfer the processing software program 2 from the image file sever a to the image file server c. Although the processing software program 2 exists at the image file server a and the mobile terminal f, the image file server a has been selected because of the shorter transmission time from the image file server a to the image file server c. After the control unit d transmits the image file server c processing parameters, the image file server c executes the processing software program 2 on the imaging data D according to the processing parameters. After the program execution, the image file server c now transmits the processed imaging data to the control unit d in the step S64 of FIG. 8. Assuming that the mobile unit m has requested the above image process on the specified imaging data, the control unit d responds to the mobile unit m that the specified imaging data and processing program both exist in the image processing entities in the step S33 of FIG. 5. Finally, the control unit d transmits the mobile unit m the processed imaging data.

With respect to the above described image processing process, the large hospital LH and the small hospital SH share certain imaging data. Assuming that the two groups of hospitals LH and SH have affiliation or cooperation, they have developed relationship for treating and referring patients. For example, if the medical problems are too complex for the small hospitals SH to offer medical services, the patients are referred to the affiliated large hospitals LH for tests and possibly treatment including major surgeries. The test results are sent back to the small hospitals SH from the large hospital LH. After the tests and the treatment at the large hospital LH, the patients go back to the originating small hospital SH for further treatment or rehabilitation. The information that is sent back from the large hospital LH is now used at the small hospitals SH during the above follow-through period.

The PACS have some redundant data storage according to the current invention. In the above described scenario, the clinical data including imaging data is stored at the large hospital LH and the small hospital SH. Since the small hospital SH generally has a smaller capacity for the data storage, it is not possible to have a complete duplicate of the imaging data. For example, the imaging data at the small hospital SH may be limited and may include only the latest set of imaging data. In the above example as described with respect to Tables 3 through 8, the imaging data D is redundantly stored in the image file server b at the large hospital LH and the image file server e at the small hospital SH. When a primary care physician at the small hospital SH requests imaging data D for his own patient from the mobile terminal f, it is determined in the above example that the image processing is optimally performed for the response time at the image file server c at the large hospital LH despite the availability of the imaging data D at the image file server e at the small hospital SH and the availability of the processing program 2 at the mobile terminal f.

It is to be understood, however, that even though numerous characteristics and advantages of the present invention have been set forth in the foregoing description, together with details of the structure and function of the invention, the disclosure is illustrative only, and that although changes may be made in detail, especially in matters of shape, size and arrangement of parts, as well as implementation in software, hardware, or a combination of both, the changes are within the principles of the invention to the full extent indicated by the broad general meaning of the terms in which the appended claims are expressed.

What is claimed is:

1. A method of archiving, processing and communicating imaging data over a network, comprising the steps of:
    storing processing software programs at a second device on the network;
    storing imaging data at a first device on the network;
    requesting the second device for information on a medical image from a third device on the network;
    requesting a process to be performed on imaging data for the requested medical image from the third device if the imaging data needs to be processed;
    transferring from the second device the information to the first device;
    transferring from the second device a selected one of the processing software programs associated with the requested process to the first device if the process has been requested; and
    executing the transferred processing software program to process the imaging data at the first device to generate processed imaging data for a processed medical image if the process has been requested.

2. The method of archiving, processing and communicating imaging data according to claim 1 further comprising an additional step of determining a storage location of the imaging data for the requested medical image.

3. The method of archiving, processing and communicating imaging data according to claim 1 further comprising additional steps of:
    transferring the processed imaging data to the third device; and
    displaying the processed medical image according to the processed imaging data at the third device.

4. The method of archiving, processing and communicating imaging data according to claim 1 further comprising additional steps of:
    transferring the imaging data for the requested medical image to the third device; and
    displaying the requested medical image at the third device.

5. A method of archiving, processing and communicating imaging data over a network, a mobile device on the network storing processing software programs, a first device on the network storing imaging data and associated information, a second device on the network storing processing software programs and imaging data, comprising the steps of:
    requesting the first device for the associated information from the mobile device;
    displaying the associated information at the mobile device;
    selecting at least one medical image based upon the associated information at the mobile device;
    receiving at the mobile device a portion of imaging data for the selected medical image from the first device;
    selecting at the mobile device a process to be performed by one of the processing software programs on the imaging data;
        inquiring of the second device about the existence of the selected medical image and the software program corresponding to the selected process at the second device to receive an inquiry result;
    transferring to the second device from the mobile device a combination of information on the selected medical image and the software program for the selected process based upon the inquiry result; and
    executing the transferred software program to process the imaging data for the selected medical image at the second device to generate processed imaging data.

6. The method of archiving, processing and communicating imaging data according to claim 5 further comprising an additional step of determining a storage location of the imaging data for the selected medical image.

7. The method of archiving, processing and communicating imaging data according to claim 5 further comprising additional steps of:
    transferring the processed imaging data to the mobile device; and
    displaying the processed medical image according to the processed imaging data at the mobile device.

8. The method of archiving, processing and communicating imaging data according to claim 5 wherein the second device includes a plurality of image file servers, the inquiry result indicating at least one of the image file servers.

9. The method of archiving, processing and communicating imaging data according to claim 8 wherein transferring to the one of the image file servers as indicated in the inquiry result from the mobile device the combination of the information on the selected medical image and the software program for the selected process.

10. The method of archiving, processing and communicating imaging data according to claim 5 further comprising an additional step of determining as to whether or not the process is externally performed at the second device on the network to generate a decision result, wherein in response to the decision result, said inquiring step is performed.

11. A method of archiving, processing and communicating imaging data over a network, comprising the steps of:
    maintaining second information on processing software programs on the network;
    maintaining first information on a plurality of medical imaging data on the network;
    requesting the first information on a selected one of the medical imaging data located at a first device on the network;
    requesting the second information on a selected one of the processing software programs located at a second device to be performed on the selected imaging data;
    comparing the first information to the second information to generate a comparison result indicative of either the selected medical imaging data or the selected processing software program is to be transferred;

transferring the selected medical imaging data to the second device or the selected processing software program to the first device based upon the comparison result; and executing the selected processing software program to process the selected imaging data to generate processed imaging data.

12. The method of archiving, processing and communicating imaging data according to claim 11 wherein the first information and the second information include a file size and the comparison result indicating a smaller one of the selected medical imaging data and the selected processing software program in the file size to be transferred.

13. The method of archiving, processing and communicating imaging data according to claim 11 further comprising an additional step of determining a storage location of the selected imaging data and the selected processing software program.

14. The method of archiving, processing and communicating imaging data according to claim 11 further comprising additional steps of:

transferring the processed imaging data to a third device; and displaying a processed medical image according to the processed imaging data at the third device.

15. A method of archiving, processing and communicating imaging data over a network, comprising the steps of:

maintaining first information on static elements including processing software programs and a plurality of medical imaging data on the network;

maintaining second information on dynamic elements including transmission rates on the network;

issuing a post-scanning process command including a selected one of the medical imaging data located at a first device on the network to be processed by a selected one of the processing software programs located at a second device on the network as well as a user-defined priority;

requesting the first information on the selected medical imaging data and the selected processing software program as well as the second information;

optimizing the user-defined priority based upon the first information and the second information;

transferring a combination of the selected medical imaging data and the selected processing software peogram over the network according to the optimized user-defined priority; and executing the selected processing software program to process the selected imaging data to generate processed imaging data in accordance with the optimized user-defined priority.

16. The method of archiving, processing and communicating imaging data according to claim 15 further comprising additional steps of:

generating a comparison result indicative of either the selected medical imaging data or the selected processing software program is to be transferred based upon the first information and the second information; and transferring the selected medical imaging data or the selected processing software program based upon the comparison result.

17. The method of archiving, processing and communicating imaging data according to claim 15 wherein the user-defined priority indicates a combination of the least execution time, the least network traffic and the least costs.

18. The method of archiving, processing and communicating imaging data according to claim 15 further comprising additional steps of:

transferring the processed imaging data to a third device; and displaying a processed medical image according to the processed imaging data at the third device.

19. A system for archiving, processing and communicating imaging data over a network, comprising:

a first device on the network for storing imaging data;

a second device on the network for storing processing software programs; and a third device on the network for transmitting a request to the second device for information on a medical image and a process to be performed on imaging data for the requested medical image if the imaging data needs to be processed, in response to the request, said second device transferring the information to said first device and a selected one of the processing software programs associated with the process to said first device if the process has been requested, said first device executing the transferred processing software program to process the imaging data to generate processed imaging data for a processed medical image if the process has been requested.

20. The system for archiving, processing and communicating imaging data according to claim 19 wherein said second device determines a storage location of the imaging data for the requested medical image.

21. The system for archiving, processing and communicating imaging data according to claim 19 wherein said first device transfers the processed imaging data to said third device, said third device displaying the processed medical image according to the processed imaging data at said third device.

22. The system for archiving, processing and communicating imaging data according to claim 19 wherein said first device transfers the imaging data for the requested medical image to said third device, said third device displaying the requested medical image at said third device.

23. The system for archiving, processing and communicating imaging data according to claim 19 further comprising any of one of the devices consisting of a CT scanner, a positron emission CT scanner, a MRI scanner, an X-ray device and an ultrasound scanner for collecting the imaging data.

24. The system for archiving, processing and communicating imaging data according to claim 19 wherein the processing software programs include ones that generate an input in a predetermined format to a computer aided diagnosis program, a three-dimensional image, a combined image and chronologically arranged images.

25. A system for archiving, processing and communicating imaging data over a network, comprising:

a first device on the network for storing imaging data for medical images and associated information;

a second device on the network for storing the imaging data for the medical images and processing software programs and for processing the imaging data by the processing software programs; and a mobile device on the network for storing the processing software programs, said mobile device sending an image list request to said first device to receive the associated information, said mobile device displaying the associated information for a user to select a set of imaging data for at least one medical image and one of the processing software programs, said mobile device inquiring of said second device about the existence of the selected imaging data and the selected processing software program at said second device to receive an inquiry result, said mobile device transferring to said second device a combination of the selected imaging data and the selected processing software program based upon the inquiry result, said second device executing the transferred processing software program to process the selected imaging data to generate processed imaging data.

26. The system for archiving, processing and communicating imaging data according to claim 25 wherein said mobile device displays the selected medical image before the user selects one of the processing software programs.

27. The system for archiving, processing and communicating imaging data according to claim 25 wherein said second device transfers the processed imaging data to said mobile device, said mobile device displaying a processed medical image according to the processed imaging data at the mobile device.

28. The system for archiving, processing and communicating imaging data according to claim 25 further comprising any of one of the devices consisting of a CT scanner, a positron emission CT scanner, a MRI scanner, an X-ray device and an ultrasound scanner for collecting the imaging data.

29. The system for archiving, processing and communicating imaging data according to claim 25 wherein the processing software programs include ones that generate an input in a predetermined format to a computer aided diagnosis program, a three-dimensional image, a combined image and chronologically arranged images.

30. The system for archiving, processing and communicating imaging data according to claim 25 wherein said second device further comprises a plurality of image file servers, the inquiry result indicating at least one of the image file servers.

31. The system for archiving, processing and communicating imaging data according to claim 30 wherein said mobile device transfers to the one of the image file servers as indicated in the inquiry result a combination of information on the selected imaging data and the selected processing software program.

32. The system for archiving, processing and communicating imaging data according to claim 25 wherein said mobile device determines as to whether or not the process is externally performed at said second device to generate a decision result, based upon the decision result, said mobile device inquiring of said second device about the existence of the selected imaging data and the selected processing software program.

33. A system for archiving, processing and communicating imaging data over a network, comprising:
a first device on the network for storing imaging data and optionally processing the imaging data;
a second device on the network for storing processing software programs and optionally processing the imaging data;
a database on the network for maintaining first information on the processing software programs and second information on a plurality of the medical imaging data on the network; and
a third device on the network for requesting the second information on a selected one of the medical imaging data that is located at said first device and the first information on a selected one of the processing software programs that is located at said second device to be performed on the selected imaging data, said third device comparing the first information to the second information to generate a comparison result indicative of either the selected medical imaging data or the selected processing software program is to be transferred, said first device transferring the selected medical imaging data to said second device based upon the comparison result, said second device transferring the selected processing software program to said first device based upon the comparison result, said first device or said second device executing the selected processing software program to process the selected imaging data to generate processed imaging data based upon the comparison result.

34. The system for archiving, processing and communicating imaging data according to claim 33 wherein the first information and the second information include a file size and the comparison result indicating a smaller one of the selected imaging data and the selected processing software program in the file size to be transferred.

35. The system for archiving, processing and communicating imaging data according to claim 33 wherein the first information and the second information include a storage location of the selected imaging data and the selected processing software program.

36. The system for archiving, processing and communicating imaging data according to claim 33 further comprising a fourth device on the network for receiving the processed imaging data and displaying a processed medical image according to the processed imaging data at the third device.

37. A system for archiving, processing and communicating imaging data over a network, comprising:
a first device on the network for storing medical imaging data;
a second device on the network for storing processing software programs;
a database on the network for maintaining first information on static elements including processing software programs and a plurality of medical imaging data on the network and for maintaining second information on dynamic elements including transmission rates on the network;
a third device on the network for issuing a post-scanning process command including a user-defined priority and a selected one of the medical imaging data located at said first device to be processed by a selected one of the processing software programs located at said second device, said third device requesting the first information on the selected medical imaging data and the selected processing software program as well as the second information, said third device optimizing the user-defined priority based upon the first information and the second information, a combination of the selected medical imaging data and the selected processing software program being transferred over the network according to the optimized user-defined priority; the selected processing software being executed to process the selected imaging data to generate processed imaging data in accordance with the optimized user-defined priority.

38. The system for archiving, processing and communicating imaging data according to claim 37 wherein said third device generates a comparison result indicative of either the selected medical imaging data or the selected processing software program is to be transferred based upon the first information and the second information.

39. The system for archiving, processing and communicating imaging data according to claim 37 wherein the user-defined priority indicates a combination of the least execution time, the least network traffic and the least costs.

40. The system for archiving, processing and communicating imaging data according to claim 37 wherein said third device displays a processed medical image according to the processed imaging data.

* * * * *